(12) United States Patent
Shah et al.

(10) Patent No.: US 8,414,581 B2
(45) Date of Patent: Apr. 9, 2013

(54) INTERMAXILLARY FIXATION DEVICE AND METHOD OF USE

(75) Inventors: Bharat Shah, Springfield, MO (US);
Kara Childers, Grovespring, MO (US);
Keela Davis, Springfield, MO (US)

(73) Assignee: Mercy Medical Research Institute, Springfield, MO (US)

( * ) Notice: Subject to any disclaimer, the term of this patent is extended or adjusted under 35 U.S.C. 154(b) by 409 days.

(21) Appl. No.: 12/622,485

(22) Filed: Nov. 20, 2009

(65) Prior Publication Data

US 2010/0124727 A1 May 20, 2010

Related U.S. Application Data

(60) Provisional application No. 61/199,823, filed on Nov. 20, 2008.

(51) Int. Cl.
*A61B 17/56* (2006.01)
(52) U.S. Cl. ............... 606/54; 433/18; 433/19; 433/24; 606/53
(58) Field of Classification Search ............. 433/18, 433/19, 24, 215; 606/105, 53–59; 602/17, 602/902
See application file for complete search history.

(56) References Cited

U.S. PATENT DOCUMENTS

| 1,638,006 | A | * | 8/1927 | Aderer | 602/5 |
|---|---|---|---|---|---|
| 3,747,164 | A | * | 7/1973 | Fortsch | 24/16 PB |
| 4,813,869 | A | * | 3/1989 | Gatewood | 433/18 |
| 5,613,853 | A | * | 3/1997 | Chasan et al. | 433/215 |
| 5,911,574 | A | | 6/1999 | Casey | |
| 6,120,288 | A | | 9/2000 | Deslauriers | |
| 6,257,884 | B1 | | 7/2001 | Chang | |
| 6,575,741 | B2 | | 6/2003 | Campbell | |
| 2002/0068254 | A1 | | 6/2002 | Campbell | |
| 2007/0190475 | A1 | * | 8/2007 | Fore et al. | 433/2 |
| 2008/0182219 | A1 | * | 7/2008 | Spalty | 433/22 |
| 2011/0152951 | A1 | * | 6/2011 | Baker | 606/328 |

* cited by examiner

*Primary Examiner* — Eduardo C Robert
*Assistant Examiner* — Nicholas Plionis
(74) *Attorney, Agent, or Firm* — Lathrop & Gage LLP

(57) ABSTRACT

An apparatus and method for fixing a patient's jaw by using arcuate arch bars which are fastened to both the upper and lower teeth using a plurality of zip ties. The arch bars are provided with bores and zip ties are passed through these bores and fastened to the patient's teeth. Each arch bar is provided with interarch receptacles which receive and engage a zip tie. The receptacles are rotatable and are generally aligned between the upper and lower arch bars. Additional zip ties with opposed teeth are passed through the upper and lower pairs of arch bar receptacles and tightened to fix the lower jar to the upper jaw.

2 Claims, 4 Drawing Sheets

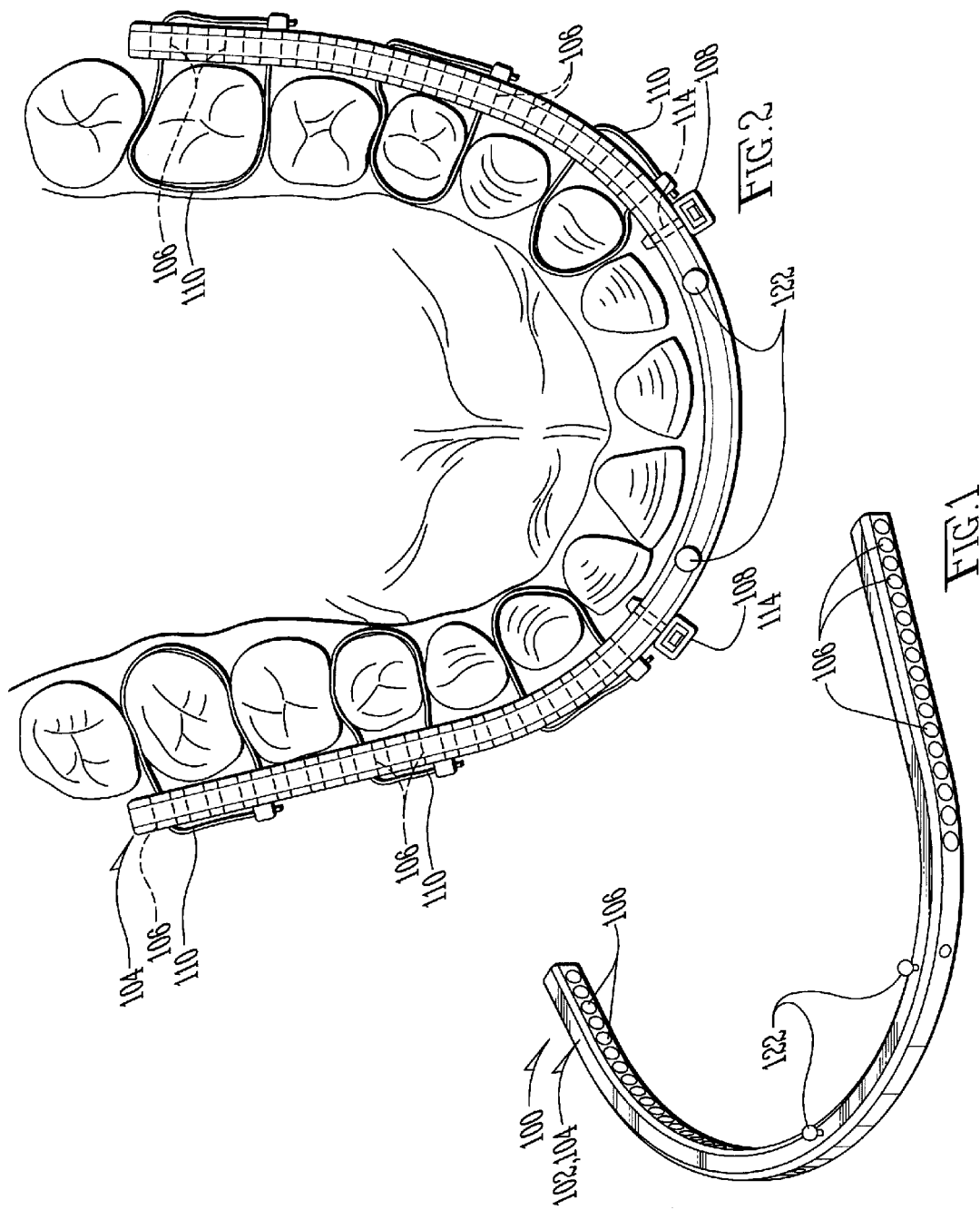

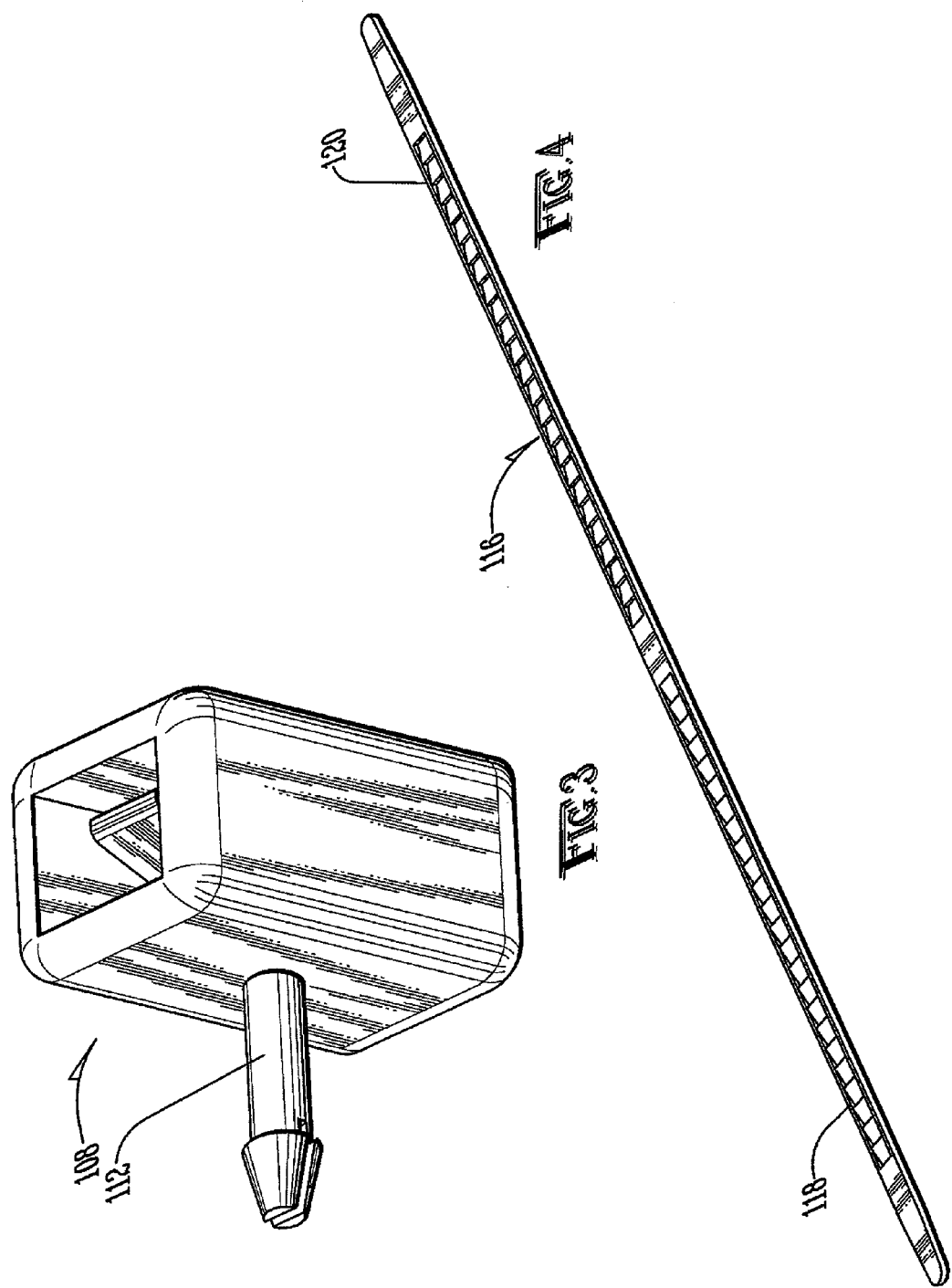

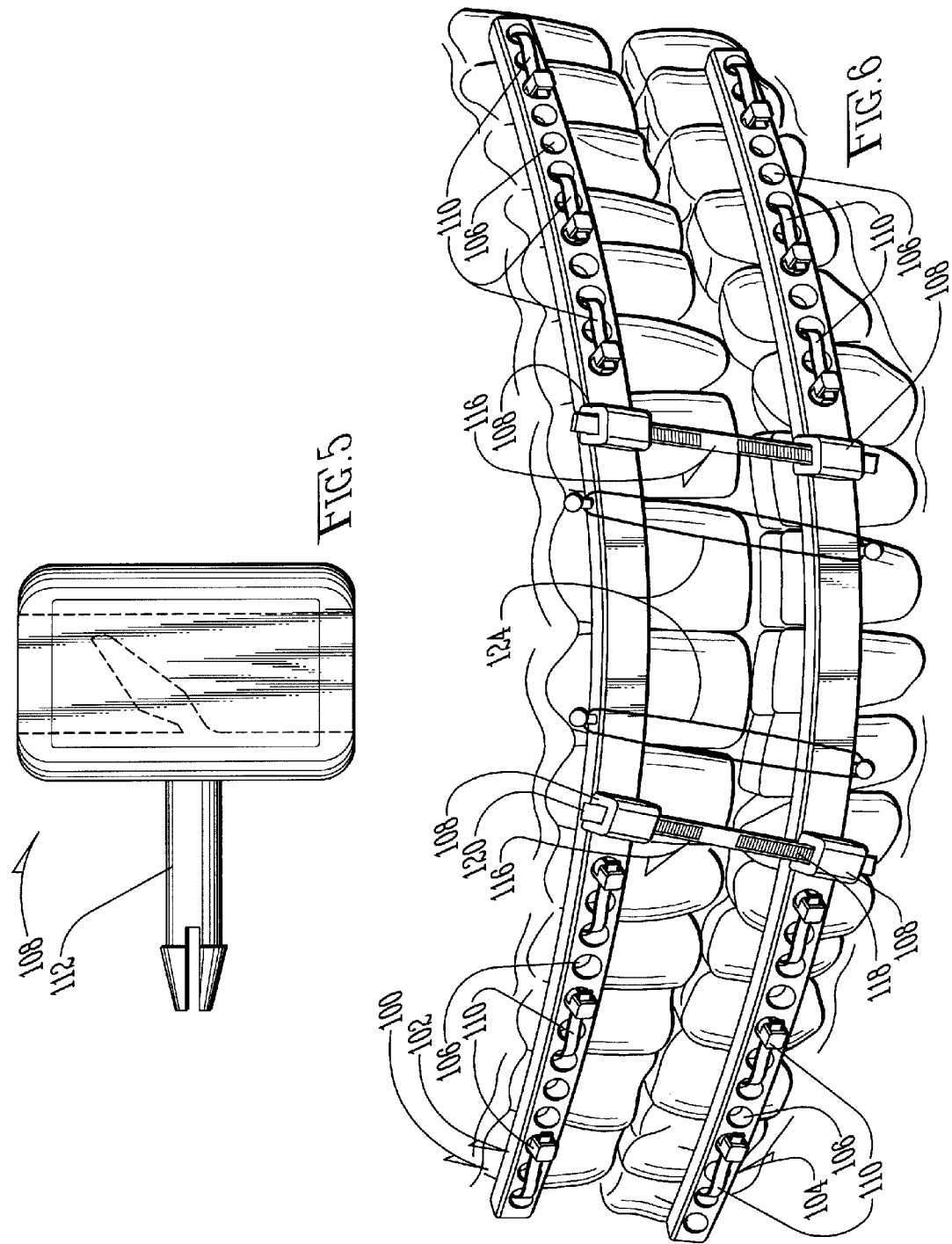

INTERMAXILLARY FIXATION DEVICE AND METHOD OF USE

RELATED APPLICATION

This application claims benefit of U.S. Patent Application Ser. No. 61/199,823, filed Nov. 20, 2008, the disclosure of which is incorporated herein by reference.

BACKGROUND

This invention relates generally to a device for providing intermaxillary fixation. This includes setting or fixing the jaw of a patient to facilitate the stabilization and healing of a fracture. The invention may also be used to fix a patient's jaw for other purposes, such as stabilizing jaws for oral, plastic, maxillofacial, ENT and trauma surgeries. The invention may also be used for the early stabilization and management of facial fractures in non-surgical settings such as by military corpsmen.

More particularly, the present invention relates to an upper and lower arch bar fastenable to a patient's teeth using pliable cable or zip ties which are easy to apply and present substantial adjustability so that the teeth may be aligned and fixed in a desired position specific to the needs of a patient.

It is well known to fasten the upper teeth to the lower teeth of a patient presenting with a broken jaw to align and fix the jaw so that it may appropriately heal. Broken jaws are relatively common and often present from sports injuries, automobile accidents, falls, and physical altercations. Jaws may also be broken for cosmetic surgery purposes and in some incidences upon the removal of diseased or cancerous jaw tissue. It is also known to wire a patient's jaw shut as a weight-loss aid in cases of extreme obesity.

In cases of trauma, it is often necessary and desirable to quickly set a broken jaw to prevent enhancement or further injury from undesirable jaw movement. This is particularly true in events such as automobile accidents and jaws which are injured in combat. For all jaw fixing procedures, it is desirable to quickly and easily fix the jaw with minimal pain to the patient, reduction of risk associated with jaw fixing and in a manner which eliminates puncture injuries to the physician and the patient.

Historically, jaws were typically fixed by boring holes through the patient's jawbone and then using metal wire to pull the lower jaw upward to the upper jaw, then twisting or otherwise fastening the wire to prevent undue movement. Other procedures included drilling into the jawbone for the placement of bolts, screws or other anchors and then wrapping wire around these fasteners to fix the jaw. Such procedures are difficult and time-consuming and present substantial risk for both patient and physician. During the application of the wires, physicians are often wounded by sharp ends of the wires. Moreover, it is very difficult to place the wire ends so that they do not cause additional injury to the patient's mouth. The use of wire materials to fix a jaw regularly cause puncture injury to both patient and physician thereby increasing the risk of blood-borne disease transmission such as HIV and hepatitis.

Various methods have been undertaken to avoid the use of metal wires to fix a patient's jaw. For example, small hooks have been glued to the patient's teeth and then fastened together with plastic material. One such device and procedure is disclosed in U.S. Pat. No. 6,120,288 to Deslauriers. This process, however, is time-consuming and difficult to place in some surgical settings such as in a combat hospital. Other efforts to avoid the use of wires have also resulted in products which are difficult to apply. It is necessary for any such apparatus to be installed such that the lower jaw is fixed to the upper jaw and virtually all lateral movement and up-and-down movement is eliminated. Accordingly, it is preferred that each of the patient's teeth are utilized to provide maximum area of contact and to eliminate such undesirable movement.

The total elimination of all bone screws, drilling, wire placement and the like is highly desirable as is the use of a device which is quickly and easily installed with the elimination of any significant risk of injury to patient or physician.

SUMMARY

Accordingly, the instant invention overcomes the stated drawbacks associated with related art. According to one embodiment of the present invention, an upper and lower arch bar are provided for placement against the outer surface of the patient's upper and lower teeth. Each arch bar is provided with a plurality of serially aligned lateral bores. Each arch bar is substantially U-shaped and is made from pliable material which can be substantially conformed to the patient's teeth. Each arch bar is further provided with a pair of spaced apart interarch receptacles.

In use, the upper arch bar is placed against the outer surface of the patient's teeth substantially aligning the arch bar bores with the interproximal gaps between the teeth. A small, commercially available, zip tie is passed through the interproximal space to encircle the tooth. The zip tie is passed through the adjacent interproximal space and generally outward through a bore of the arch bar. The zip tie is then fastened in a conventional manner such that the tooth adjacent the arch bar is completely encircled and as the zip tie is fastened, the arch bar is urged against the tooth and generally fastened thereto. As few as two zip ties can be used to secure the interarch bar to the upper teeth and two for the lower teeth. It is understood, however, that more teeth may be encircled to adjust fit. The physician fastens the arch bar to each of the patient's teeth by the method described above.

The upper arch bar is fastened to the patient's upper teeth and the lower arch bar is likewise fastened to the lower teeth. The upper arch bar and lower arch bar are then fastened together through the interarch receptacles to secure the jaw in a closed position. During placement and positioning, it is important to substantially align the interarch receptacles of the upper and lower arch bars. The interarch receptacles are substantially similar in construction and configuration to the female portion of a standard zip tie. It is preferred that the interarch receptacles are fastened to the arch bar with a pin which allows them to freely rotate. This rotation allows the interarch receptacles of the upper arch bar to be substantially aligned with the interarch receptacles of the lower arch bar.

Orientation of the arch bars is specific in that the interarch receptacles only function appropriately in one orientation similar to the receptacle of a standard zip tie. In other words, if the male portion, or ratchet-serrated strap, of a zip tie is passed in the wrong direction into the female receptacle, or ratchet, of the zip tie it will not fasten because the teeth present on the zip tie or serrated strap cannot engage with the stay bar in the receptacle or ratchet. If, however, the interarch receptacles are rotatable, the arch bar does not have to be installed in a specific top to bottom orientation. The physician can simply rotate the interarch receptacle so that it is oriented in the direction to function with a zip tie.

A zip tie is then passed through the interarch receptacle of the upper arch bar into the interarch receptacle of the lower arch bar. A zip tie is provided for this specific purpose which has opposed teeth. Specifically, the zip tie for this use has a first-end and a second-end. A plurality of teeth, commonly found on zip ties, is oriented in a first direction on the first end of the zip tie and in the opposed direction on the second end of the zip tie. Accordingly, when this zip tie is placed in the interarch receptacles and the lower jaw is urged upward to the upper jaw, the interarch receptacles engage the respective ends of the zip tie and thereby lock the lower arch bar to the upper arch bar. The physician then trims any loose ends of each zip tie to avoid puncture, aggravation or inflammation of the patient's mouth. In the event the zip ties become loose or break, they are easily replaced. Moreover, with the jaw-fixing procedure complete, the apparatus is quickly and easily removed by simply cutting each of the zip ties with scissors.

Because the lower jaw is fastened to the upper jaw by the positioning of the reciprocal zip ties and interarch receptacles, in the event the patient's mouth must be quickly opened, this is achieved by simply cutting the two reciprocal zip ties. This allows the patient's mouth to be open much quicker than if it were fastened by any of the prior methods.

BRIEF DESCRIPTION OF THE DRAWINGS

FIG. 1 is a perspective view of an arch bar of one embodiment of the invention.

FIG. 2 is a top view of an arch bar installed on the teeth of a patient.

FIG. 3 is a perspective view of a rotatable interarch receptacle.

FIG. 4 is a plan view of an opposed zip tie for use with the interarch receptacles.

FIG. 5 is an end view of a rotatable interarch receptacle.

FIG. 6 is a partial front view of a patient's mouth with the upper and lower arch bars fastened together with an opposed zip tie through the pairs of interarch receptacles.

Figure 7:
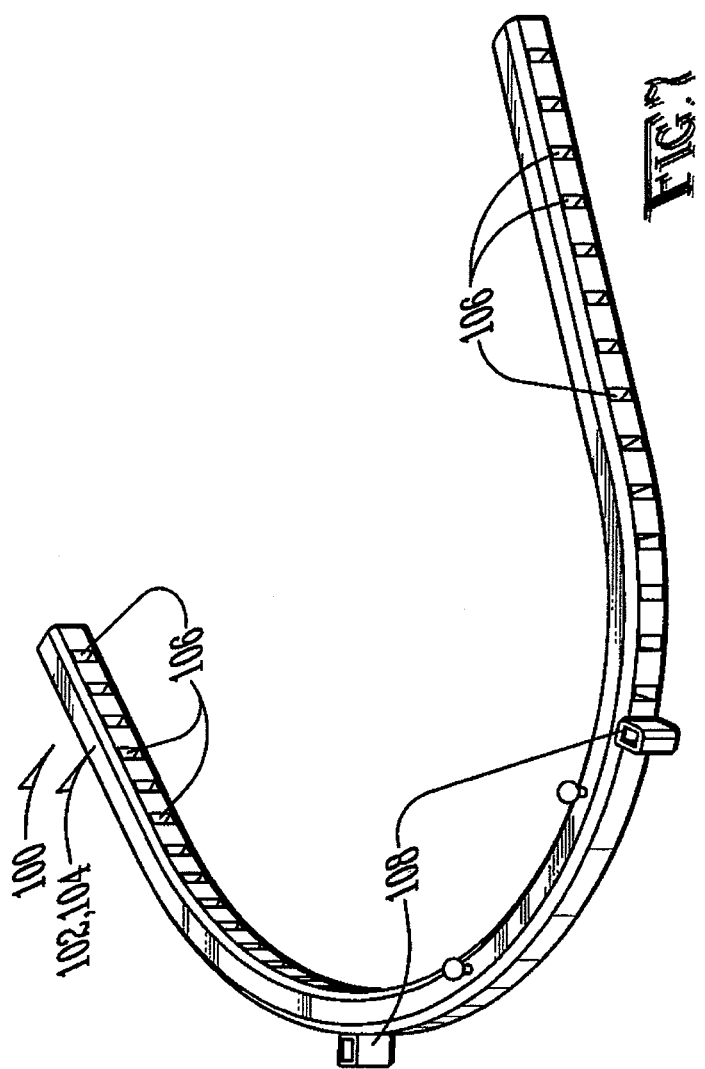
FIG. 7 is a perspective view of a second embodiment of an arch bar.

DETAILED DESCRIPTION OF PREFERRED
EMBODIMENT OF THE INVENTION

Referring generally to the drawings, an apparatus 100 is provided for fixation of a patient's lower jaw to the upper jaw. According to one embodiment of the present invention, an upper bar 102 and lower arch bar 104 are provided for placement against the outer surface of the patient's upper and lower teeth. As best shown in FIGS. 1, 2 and 7, each arch bar 102, 104 are provided with a plurality of serially aligned lateral bores 106. The shape of the bores can vary as shown, such as round or rectangular for different applications or to accommodate different securement materials. Each arch bar 102, 104 are substantially U-shaped and are made from pliable material which can be substantially conformed to the patient's teeth. The components of the apparatus may be formed of a variety of materials, including, but not limited to various plastics and polymers.

Each arch bar 102, 104 is preferably provided with a pair of spaced apart interarch receptacles 108. It is preferred that the upper arch bar 102 and lower arch bar 104 are identical in manufacture to reduce costs and enhance the ease of installation.

In use, the upper arch bar 102 is placed against the outer surface of the patient's teeth substantially aligning the arch bar bores 106 with the interproximal gaps between the teeth. A small, commercially available, zip tie 110, or similar binding mechanism, is passed through one bore 106 then through the interproximal space. The zip tie 110 is then wrapped around the adjacent tooth, passed generally outward through the next interproximal space and through the closest bore 106. Thusly, the zip tie 110 substantially encircles the tooth. The zip tie 110 is then fastened in a conventional manner such that the tooth adjacent the arch bar 102 or 104 is completely encircled and as the zip tie 110 is fastened, the arch bar 102 or 104 is urged against the tooth and generally fastened thereto. It is preferred that the end of the zip tie presenting through the zip tie ratchet or receptacle is oriented such that it lies substantially parallel the patient's teeth to avoid undesirable contact between the tie and the inner cheek or mucous membrane of the mouth.

The physician fastens the arch bar 102 or 104 to each of the patient's teeth by the method described above. The upper arch bar 102 is fastened to the patient's upper teeth and the lower arch bar 104 is likewise fastened to the lower teeth. During placement and positioning, it is important to substantially align the interarch receptacles 108 of the upper and lower arch bars 102, 104. The interarch receptacles 108 are substantially similar in construction and configuration to the female, or ratchet, portion of a standard zip tie. As shown in FIGS. 3 and 5 it is preferred that the interarch receptacles 108 are provided with a pin 112 which rotatably fastens into a socket 114 provided on each arch bar 102, 104. This rotation allows the interarch receptacles 108 of the upper arch bar 102 to be substantially aligned with the interarch receptacles 108 of the lower arch bar 104. Each arch bar 102, 104 is preferably provided with two sockets 114 for receipt of a spaced-apart pair of interarch receptacles 108.

Unless the interarch receptacles 108 are rotatable, the orientation of the arch bars is specific in that the interarch receptacles 108 only function appropriately in one direction similar to the receptacle of a standard zip tie. In other words, if the male portion of a zip tie is passed in the wrong direction into the female receptacle of the zip tie it will not fasten because the teeth present on a zip tie cannot engage with the stay bar in the receptacle. However, where the interarch receptacles 108 are rotatable, the physician does not have to install the arch bars 102, 104 in a specific top to bottom orientation. The physician can simply rotate the interarch receptacle 108 within the socket 114 so that it is oriented in the desired and necessary direction to function with a zip tie end.

An opposed zip, or cable, tie 116 is then passed through the interarch receptacle 108 of the upper arch bar 102 into the interarch receptacle 108 of the lower arch bar 104. An opposed zip tie 116 is provided for this specific purpose which has opposed teeth. Specifically, the opposed zip tie 116 for this use has a first-end 118 and a second-end 120 as best shown in FIG. 4. As shown, a plurality of teeth or ratchet serrations, commonly found on zip ties, are oriented in a first direction on the first end 118 of the zip tie and in the opposed direction on the second end 120 of the zip tie. Accordingly, when this opposed zip tie 116 is placed in the interarch receptacles 108 and the lower jaw is urged upward to the upper jaw, the interarch receptacles 108 engage the respective ends of the opposed zip tie 116 and thereby locks the lower arch bar 104 to the upper arch bar 102. Once the installation of the apparatus 100 is complete, as shown in FIG. 6, the physician then trims any loose ends of each zip tie 110 and the opposed zip tie 116 to avoid puncture, aggravation or inflammation of the patient's mouth. In the event the any of the zip ties become loose or break, they are easily replaced. Moreover, with the jaw-fixing procedure complete, the apparatus is quickly and easily removed by simply cutting each of the zip ties. Further, the patient can easily separate the jaws by cutting the ties.

Because the lower jaw is fastened to the upper jaw by the positioning of the opposed zip ties 116 and interarch receptacles 108, in the event the patient's mouth must be quickly opened, this is achieved by simply cutting the two opposed zip ties 116. This allows the patient's mouth to be open much quicker than if it were fastened by any of the prior methods. It may also be beneficial to utilize resilient zip ties to fasten the jaws where rigid fixation is not desired, for example, during the treatment of a mandibular joint injury where limited joint movement is preferred.

As shown in FIGS. 1, 6 and 7, a pair of spaced apart retention knobs 122 may be formed on a surface of each arch bar 102,104. The arch bars are installed with the knobs 122 oriented upward on the upper teeth and downward on the lower teeth. These knobs 122 allow a physician or a patient to use rubber bands 124 or similar fasteners to connect the upper arch bar 102 to the lower arch bar 104. Rubber bands, or similar fasteners are often used to secure orthodontic appliances. Common appliances such as braces often include hangers or clips onto which rubber bands are attached. The knobs 122 provide fastening points for similar application or use of rubber bands 124. These can be used to supplement the opposed zip ties 116 or in place of the opposed zip ties 116. Because the interarch receptacles 108 can be mounted and swiveled, it is primarily important to orient the arch bars correctly to position the knobs 122 when it is anticipated that bands will be used alone or to supplement the interarch ties 116. In the event that it is known that the knobs 122 will not be used, the orientation of the arch bar becomes irrelevant.

While the invention has been illustrated and described in detail in the drawings and the foregoing description, the same is to be considered illustrative and not restrictive of the character. It is to be understood that changes, modifications and equivalents that come within the scope and spirit of the invention as defined by the following claims are also desired to be protected.

What is claimed is:

1. An apparatus for fastening a patient's upper jaw and lower jaw together comprising:
    an upper arch bar including a plurality of lateral bores;
    a lower arch bar including a plurality of lateral bores;
    at least one rotatable upper interarch receptacle;
    at least one rotatable lower interarch receptacle;
    a plurality of arch bar fasteners for attaching the upper arch bar to the upper jaw and the lower arch bar to the lower jaw; and
    at least one interarch fastener for fastening the at least one rotatable upper interarch receptacle and the at least one rotatable lower arch receptacle, together;
    wherein the at least one rotatable upper interarch receptacle and the at least one rotatable lower interarch receptacle freely rotate to substantially align when fastened together;
    wherein each of the plurality of arch bar fasteners is secured through two lateral bores in the upper arch bar, or through two lateral bores in the lower arch bar;
    wherein one or more fasteners of the plurality of arch bar fasteners comprises a strap having a length and ratchet serrations extending substantially along the length of the strap from a first end thereof to a second end thereof, and a ratchet attached to the second end thereof for receiving and securing the first end of the strap;
    wherein the at least one interarch fastener is secured to one interarch receptacle on the upper arch bar and one interarch receptacle on the lower arch bar;
    the at least one interarch fastener comprising a linear strap with the ratchet serrations, wherein both the rotatable upper interarch receptacle and the rotatable lower interarch receptacle incorporate a ratchet for receiving and securing the ratchet serrations on the interarch fastener;
    the linear strap of the at least one interarch fastener further comprising:
        a front side including first and second ratchet engaging surfaces disposed proximate opposing ends of the strap, for engaging ratchet portions of the rotatable upper interarch receptacle and the rotatable lower interarch receptacle, the first ratchet engaging surface including ratchet serrations oriented in a first direction and the second ratchet engaging surface including ratchet serrations oriented in a second direction, opposite the first direction; and
        a back side having a smooth surface.

2. The apparatus of claim 1 wherein the at least one interarch fastener is an opposed cable tie.

* * * * *